United States Patent [19]

Rephaeli et al.

[11] Patent Number: 6,043,277
[45] Date of Patent: Mar. 28, 2000

[54] RETINOYLOXY (ALKYL-SUBSTITUTED) METHYL BUTYRATES USEFUL FOR THE TREATMENT OF GASTROINTESTINAL DISORDERS, CUTANEOUS ULCERS AND WOUNDS

[75] Inventors: Ada Rephaeli, North Caldwell, N.J.; Abraham Nudelman, Rehovot, Israel

[73] Assignees: Bar-Ilan University, Ramat-Gan; Kupat Holim Health Institution of the General Federation of Labor, Tel Aviv, both of Israel

[21] Appl. No.: 08/944,906

[22] Filed: Oct. 6, 1997

Related U.S. Application Data

[60] Division of application No. 08/674,481, Jul. 2, 1996, which is a continuation-in-part of application No. 08/306,422, Sep. 16, 1994, Pat. No. 5,710,176.

[51] Int. Cl.$^7$ .................................................. A61K 31/225
[52] U.S. Cl. .............................................................. 514/548
[58] Field of Search ............................................. 514/548

[56] References Cited

U.S. PATENT DOCUMENTS

| | | | |
|---|---|---|---|
| 3,882,244 | 5/1975 | Lee ........................................... | 424/318 |
| 4,054,589 | 10/1977 | Bollag et al. ............................. | 260/408 |
| 4,105,681 | 8/1978 | Bollag et al. ............................. | 260/404 |
| 4,215,215 | 7/1980 | Bollag et al. ............................. | 542/427 |
| 4,677,120 | 6/1987 | Parish et al. .............................. | 514/549 |
| 4,885,311 | 12/1989 | Parish et al. .............................. | 514/549 |
| 4,900,478 | 2/1990 | Gross ........................................ | 260/408 |
| 5,124,356 | 6/1992 | Purcell et al. ............................ | 514/529 |
| 5,158,773 | 10/1992 | Gross ........................................ | 424/406 |

FOREIGN PATENT DOCUMENTS

| 449099 | 10/1991 | European Pat. Off. . |
|---|---|---|
| 9006751 | 6/1990 | WIPO . |

OTHER PUBLICATIONS

Feldman et al (1993) N. Engl. J. Med. 329: 177–89.
Collins SJ, et al., Int.J. Cancer 25: 213–218(1980).
Strickland S., et al., Cell 15: 393–403 (1978).
Chomienne, et al., Blood 76: No. 9 1710–1717 (1990).
Wright DG., Blood 67: No. 1 334–337 (1987).
Toscani, et al., Oncogene Res. 3: 228–238 (1988).
Prasad KN., et al., Biochem. Cell. Biol. 68: No. 11 1250–1255 (1992).
Rabizadeh E., et al., FEBS Lett. 328: No. 3 225–229 (1993).
Breitman, et al., Cancer Res. 50: 6268–6273 (1990).
Warrell RP. Jr., et al., N. Engl. J. Med. 324/20: 1385–1393 (1991).
Adamson PC., et al., Journal of the National Cancer Institute 85/12: 993–996 (1993).
Reese et al. (1985) Cancer Res. 45: 2308–2313.
Reiss et al. (1986) Cancer Treat. Rep. 70:201–218.

*Primary Examiner*—Laura L. Stockton
*Attorney, Agent, or Firm*—Kenyon & Kenyon

[57] ABSTRACT

This invention relates to the novel compounds of Formula (I) and pharmaceutical compositions containing same, to methods of treating, preventing or ameliorating cancer and other proliferative diseases in a subject in need of such treatment comprising administering a compound of Formula (I) and pharmaceutically-acceptable salts and prodrugs thereof.

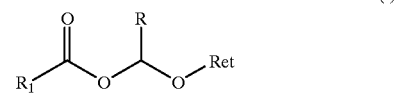

Formula (I)

The compounds of the invention are also useful in methods of ameliorating wrinkles, inducing wound healing, treating cutaneous ulcers and treating gastrointestinal disorders.

11 Claims, 1 Drawing Sheet

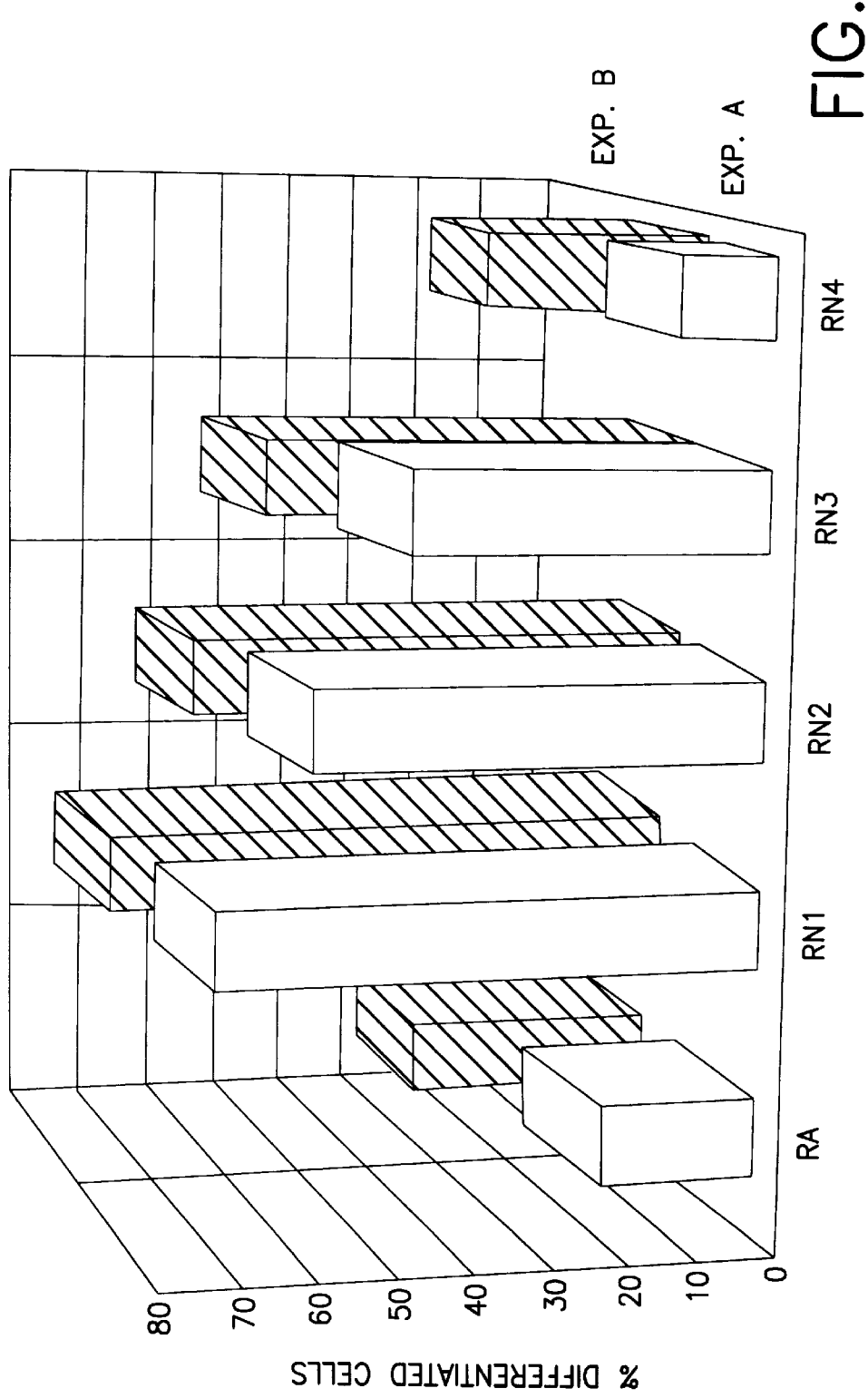

RETINOYLOXY (ALKYL-SUBSTITUTED) METHYL BUTYRATES USEFUL FOR THE TREATMENT OF GASTROINTESTINAL DISORDERS, CUTANEOUS ULCERS AND WOUNDS

This application is a continuation of application Ser. No. 08/674,481, filed on Jul. 2, 1996, which is a continuation-in-part of U.S. Ser. No. 08/306,422 filed Sep. 16, 1994, now U.S. Pat. No. 5,710,176.

FIELD OF THE INVENTION

The present invention is directed to retinoyloxy (substituted) methyl butyrates and pharmaceutically acceptable salts thereof, to pharmaceutical compositions comprising said compounds, and to methods of treating cancer and other proliferative diseases in a subject in need of such treatment comprising administering to said subject the compound or composition comprising compounds of Formula (I), or a pharmaceutically acceptable salt thereof. The compounds of the invention are also useful in methods of ameliorating wrinkles, inducing wound healing, treating cutaneous ulcers and treating gastrointestinal disorders.

BACKGROUND OF THE INVENTION

The uncontrolled proliferation of cancer cells is accompanied by the increase of immature cell populations. (Bloch, A., *Cancer Treat. Rev.* 68:199–205, 1984.) Although cancer cells are characterized by a marked capacity to proliferate and a limited capacity to differentiate under normal homeostatic conditions, experimental evidence has demonstrated that neoplastic cells can be induced to differentiate, indicating that malignant processes can be altered or, at least partially, reversed.

The retinoids are a family of compounds consisting of vitamin A, retinoic acid (RA) and related derivatives. They play a pivotal role in normal development of endodermally-, mesodermally- and ectodermally-derived tissues. (Umesono K. et al., *Nature* 336:262–265, 1989).

The mode of action of RA has been extensively studied. In the cytoplasm, RA binds to the cytoplasmic RA-binding protein, whose role in mediating RA effects is unclear. In the nucleus, RA binds to the RA receptors (RAR-α, -β, -γ). The RAR/RA complex binds to a specific DNA sequence, as demonstrated by electrophoretic mobility shift (Rochette-Egly et al., *J. Cell. Biol.* 115:535–545, 1991), leading to transcription of RA target genes. RAR-α has been shown to be involved with growth and differentiation of myeloid cells in vitro. For instance, patients with acute promyelocytic leukemia have a characteristic (15:17) translocation with the breakpoint in the region of RAR-α coding sequence. Thus, mRNA for RAR are a useful tool to study potential antitumor drugs.

RA was reported to induce differentiation and arrest proliferation in a wide spectrum of cancer cells in vitro and in vivo, including patients with leukemia, myelodysplastic syndromes and solid tumors. For instance, Collins et al. *Int. J. Cancer* 25:213–218, 1980, have shown that the human promyelocytic leukemia cell line HL-60 can be induced to differentiate by RA and express cellular and molecular characteristics of granulocytes. (Umesono et al.) Emergence of differentiated features include elevated protein kinase C and intracellular lysosomal activities. Strickland et al., have shown that exposure of the teratocarcinoma cell line F9 to RA caused differentiation to visceral endoderm (*Cell* 15:393–403, 1978).

Several retinoids have achieved significant activity in the reversal of head and neck, skin, and cervical premalignancy and in prevention of second primary tumors associated with head and neck, skin and non-small lung cancer. Lippman et al. (*J. Cell. Biochem.* 22:1, 1995) have demonstrated chemoprevention activity of retinoids in aerodigestive tract carcinogenesis. This was tested in the two-stage mouse lung carcinogenesis model described by Nishimo, *J. Cell. Biochem.* 22:231, 1995.

Strickland et al., demonstrated that in an in vivo murine model, orally administered RA increased the survival of mice bearing F9 tumors in a dose-dependent manner (*Dev. Biol.* 78:76–85, 1980). The tumors of the RA-treated mice were much smaller in comparison to untreated animals and showed morphological and biochemical evidence of differentiation.

Because of the low therapeutic index of RA, its isomer, all-trans RA (ATRA), has been extensively studied. At 1 $\mu$m, ATRA has been shown to cause differentiation in vitro as demonstrated by measuring an increase of nitro-blue tetrazolium (NBT) reduction (Chomienne et al., *Blood* 76:1710–1717, 1990).

Evidence has also accumulated for in vivo induction of differentiation by ATRA treatment. One morphological feature indicating differentiation of promyelocytic leukemia cell populations to mature cells is the appearance of Auer rods (homogenous crystallinic red-stained structure). Treatment of acute promyelocytic leukemia (APL) patients with ATRA resulted in complete remissions without bone-marrow hypoplasia. The presence of Auer rods in the maturing cells of these patients confirmed the differentiating activity of ATRA.

Due to results from clinical and laboratory studies, ATRA is now considered to be a first line therapeutic agent for promyelocytic leukemias (Wright D.G., *Blood* 67:334–337, 1987). However, the achievement of remission induced by ATRA tends to be brief and may be explained by rapid clearance in patients resistant to ATRA (Muindi et al. *Cancer Res.* 52:2138–2142, 1992). Moreover, Adamson et al. reports that patients orally administered ATRA had highly variable absorption of the drug (*J. Natl. Can. Inst.,* 85(12):993–996, 1993). Hence, maintenance of effective plasma concentrations and toxicity are problems associated with retinoid treatments (Adamson et al., *J. Natl. Cancer Inst.* 85:993–996, 1993).

Butyric acid (BA) is a non-toxic natural product. It is supplied to mammals from two main sources: 1) the diet, mainly from dairy fat, 2) as a major product of bacterial fermentation of unabsorbed carbohydrates in the colon, where it reaches mM concentrations (Cummings J. H., *Gut* 22:763–779, 1982; Leder A. et al., *Cell* 5:319–322, 1975).

BA has been known for nearly the last three decades to be a potent differentiating and antiproliferative agent in a wide spectra of neoplastic cells in vitro (Prasad N. K., *Life Sci.* 27:1351–1358, 1980). In cancer cells, BA is reported to induce cellular and biochemical changes, e.g., in cell morphology, enzyme activity, receptor expression and cell-surface antigens (Nordenberg J. et al., *Exp. Cell Res.* 162:77–85, 1986; Nordenberg J. et al., *Br. J. Cancer* 56:493–497, 1987; and Fishman P. H. et al., *J. Biol. Chem.* 254:4342–4344, 1979).

Although BA or its sodium salt (sodium butyrate, SB) has been the subject of numerous studies, its mode of action is unclear. The most specific effect of butyric acid is inhibition of nuclear deacetylase(s), resulting in hyper acetylation of histones H3 and H4 (Riggs M. G., et al., *Nature*

263:462–464, 1977). Increased histone acetylation, following treatment with BA has been correlated with changes in transcriptional activity and the differentiated state of cells (Thorne A. W. et al., *Eur. J. Biochem.* 193:701–713, 1990). BA also exerts other nuclear actions, including modifications in the extent of phosphorylation (Boffa L. C. et al., *J. Biol. Chem.* 256:9612–9621, 1981) and methylation (Haan J. B. et al., *Cancer Res.* 46:713–716, 1986). Other cellular organelles, e.g., cytoskeleton and membrane composition and function, have been shown to be affected by BA (Bourgeade M. F. et al., *J. Interferon Res.* 1:323–332, 1981). Modulations in the expression of oncogenes and suppressor genes by BA were demonstrated in several cell types. Toscani et al., reported alterations in c-myc, p53 thymidine kinase, c-fos and AP2 in 3T3 fibroblasts (*Oncogene Res.* 3:223–238, 1988). A decrease in the expression of c-myc and H-ras oncogenes in B16 melanoma and in c-myc in HL-60 promyelocytic leukemia were also reported (Prasad K. N. et al., *Biochem. Cell Biol.* 68:1250–1255, 1992; and Rabizadeh E. et al., *FEBS Lett.* 328:225–229, 1993). However, BA is normally metabolized rapidly and has a very short half-life in vivo, thus the achievement and maintenance of effective plasma concentrations are also problems associated with BA.

Apoptosis is the physiological mechanism for the elimination of cells in a controlled and timely manner. Organisms maintain a delicate balance between cell proliferation and cell death, which when disrupted can tip the balance between cancer, in the case of over accumulation of cells, and degenerative diseases, in the case of premature cell losses. Hence, inhibition of apoptosis can contribute to tumor growth and promote progression of neoplastic conditions. BA is known to induce cell death via apoptosis.

Synergistic anti-proliferative and differentiating effects of combinations of RA with other differentiating agents or cytokines have been suggested. For instance, Breitman et al., demonstrated that BA alone induced differentiation of HL-60 cells, a human promyelocytic cell line, with an ED50 of 444 µM, and RA alone induced HL-60 cells with an ED50 at 0.13 µM. However, the combination of about 28 nM RA with BA reduced the ED50 value for BA from about 400 to about 75 µM, a dose reduction index value of about 6-fold (*Cancer Res.* 50:6268–6273, 1990). Based on his study, Breitman suggested that RA might be useful in combination with other agents in the treatment of some leukemias. However, treatment with either BA or RA alone or in combination will continue to have the problems of toxicity, as well as achieving and maintaining effective plasma concentrations.

Others have studied conjugated RA compounds. For instance, Parish, U.S. Pat. No. 4,677,120 (issued Jun. 30, 1987) and PCT Application No. WO 90/06751 disclose the use of compounds of formulas A or B:

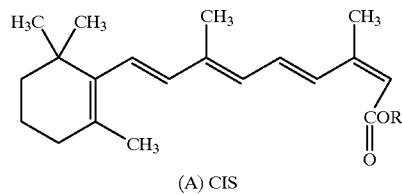

(A) CIS

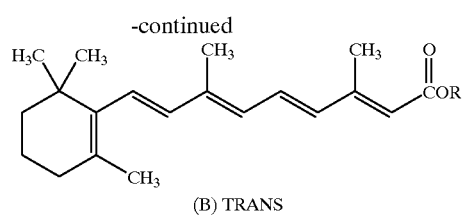

(B) TRANS wherein R is $CR_2'''OC(=O)CR_3'$, R' is H or $C_1$–$C_6$ alkyl, R''' is R' or the hydrocarbon backbone of fatty acids, for affecting the reduction and reversal of photo aging and skin cancer. This application does not disclose or enable methods of the present invention.

Gross, U.S. Pat. No. 4,900,478 (issued Feb. 13, 1990), discloses, inter alia, all-trans-9-4-methoxy-2,3,6-trimethylphenyl)-3,7-dimethyl-2,4,6,8-nona-tetraenoic acid and in EPO Application 0449099 discloses the use of compounds of the formula $R^1OCH(R^2)OC(O)R^3$, wherein $R^1$ is 13-cis-retinoyl, $R^2$ is alkyl and $R^3$ is alkyl or alkoxy, for the treatment of skin disorders. This application does not disclose or enable methods of the present invention.

Thus, there remains the need to identify compounds as effective as the combination of BA and RA as differentiating or anti-proliferating agents for the treatment of cancers. Such compounds need to have high potency without the problems associated with BA and RA.

This invention addresses this need and is thus directed to the novel compounds of Formula (I) and, in particular, to retinoyloxymethylbutyrate (ROBA), which are more potent than BA or RA alone or combined, to compositions comprising same and to methods of using same for the treatment of cancers and other proliferative diseases, for gastrointestinal disorders, for ameliorating wrinkles, and for wound healing. None of the references discussed above teach or suggest the compounds of Formula (I), pharmaceutical compositions containing same or the methods of using said compounds or compositions as anti-cancer and anti-proliferative agents.

SUMMARY OF THE INVENTION

Accordingly, one embodiment of the present invention is directed to the novel compounds having the Formula (I):

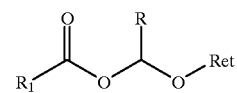

Formula (I)

wherein:

Ret is selected from the group consisting of a retinoyl group, a therapeutically active retinoid carboxy group, a therapeutically active carboxy group represented by the formula

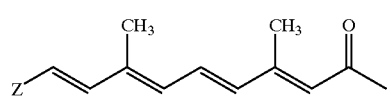

and retinoids which are C20 or C22 desmethyl vinylogs of said groups, wherein Z is a substituted or unsubstituted phenyl group, a substituted or unsubstituted naphthyl group or a cyclohexenyl group, and said phenyl or naphthyl group can be substituted with from 0 to 5 substitutents selected from the group consisting of halo, hydroxy, alkyl, alkyoxy, amino, cyano or carbalkoxy, and wherein double bonds in the polyene chain of any of said groups can have a cis or trans configuration;

R is H or saturated or unsaturated $C_1$ to $C_5$ alkyl;

$R_1$ is ethyl, n-propyl or isopropyl; and pharmaceutically acceptable salts thereof, with the proviso that when Ret is 13-cis-retinoyl and $R_1$ is n-propyl, then R cannot be H or $C_1$ to $C_5$ alkyl.

Preferred are compounds wherein Ret is trans. Specifically preferred is the compound trans-retinoyloxymethylbutyrate (ROBA). The compounds of the present invention have greater efficacy as proliferation inhibitors and differentiating agents than either BA or RA alone or a combination of BA plus RA.

Another embodiment of the present invention is drawn to pharmaceutical compositions comprising a therapeutically effective amount of a compound of Formula (I) and a pharmaceutically effective carrier or diluent.

A further embodiment of the present invention is directed to pharmaceutical compositions comprising a therapeutically effective amount of a combination a compound of Formula (I) or of ROBA with other anti-cancer or antineoplastic agents together with a pharmaceutically effective carrier or diluent.

Another embodiment of the present invention is directed to methods of treating, preventing or ameliorating cancer and other proliferative disorders which comprise administering a therapeutically effective amount of a compound of Formula (I) to a subject suffering from such disorders and to methods of enhancing the actions of other known antiproliferative, differentiating or oncostatic agents.

A still further embodiment of the invention is directed to a method of ameliorating wrinkles, inducing wound healing, treating cutaneous ulcers or treating a gastrointestinal disorder by administrating a therapeutically-effective amount of a compound of Formula (I) to a subject in need of such treatment. The cutaneous ulcers which can be treated in accordance with the methods of the invention include leg and decubitus ulcers, stasis ulcers, diabetic ulcers and atherosclerotic ulcers. With respect to wound healing, the compounds are useful in treating abrasions, incisions, burns, and other wounds. Gastrointestinal orders treatable by the methods of the invention include colitis, inflammatory bowel disease, Crohn's disease and ulcerative colitis.

The methods of the present invention are particularly useful for treating, preventing or ameliorating the effects of cancer and other proliferative disorders by acting as antiproliferative or differentiating agents in subjects afflicted with such anomalies. Such disorders include but are not limited to leukemias, such as acute promyelocytic leukemia, acute myeloid leukemia, and acute myelomonocytic leukemia; other myelodysplastic syndromes, multiple myeloma such as but not limited to breast carcinomas, cervical cancers, melanomas, colon cancers, Kaposi's sarcoma, ovarian cancers, pancreatic cancers, hepatocarcinomas, prostate cancers, squamous carcinomas, other dermatologic malignancies, teratocarcinomas, T-cell lymphomas, lung tumors, gliomas, neuroblastomas, peripheral neuroectodermal tumors, rhabdomyosarcomas, and prostate tumors and other solid tumors. It is also possible that compounds of Formula (I) have anti-proliferative effects on non-cancerous cells as well, and may be of use to treat benign tumors and other proliferative disorders such as psoriasis. Preferred is the method for treating or ameliorating leukemia, squamous cell carcinoma and neuroblastoma.

While it is possible to utilize the compounds in vivo as raw chemicals, it is preferable to present them as pharmaceutical compositions.

BRIEF DESCRIPTION OF THE DRAWINGS

FIG. 1 illustrates the effect of all-trans retinoids on cell differentiation in human HL-60 cells.

DETAILED DESCRIPTION OF THE INVENTION

The compounds herein described may have asymmetric centers. All chiral, diastereomeric, and racemic forms are included in the present invention. Many geometric isomers of olefins and the like can also be present in the compounds described herein, and all such stable isomers are contemplated in the present invention.

By "stable compound" or "stable structure" is meant herein a compound that is sufficiently robust to survive isolation to a useful degree of purity from a reaction mixture, and formulation into an efficacious therapeutic agent.

As used herein, "alkyl" is intended to include both branched- and straight-chain saturated or unsaturated aliphatic hydrocarbon groups having the specified number of carbon atoms. Preferably the alkyl groups of the invention have from 1 to 5 carbon atoms.

As used herein a therapeutically active retinoid is a compound which exhibits a biological action similar to retinoic acid (i.e., similar to vitamin A acid). Hence retinoids include those compounds, synthetic or natural, which have one or more of the therapeutic activities known for retinoic acid. Such activities include but are not limited to binding to and activating retinoic acid receptors, treating and preventing cancer and other proliferative disorders, acting as differentiating agents or anti-proliferatives agents and anti-tumor activity. Thus, as embodied herein Ret of Formula (I) is a retinoid carboxyl group of a therapeutically active retinoid. Moreover, Ret includes compounds of the formula

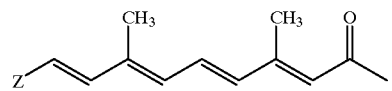

where Z is as defined above. Examples of retinoids contemplated by the invention can be found in U.S. Pat. Nos. 4,476,056; 4,105,681; 4,215,215; 4,054,589 and 3,882,244. Retinoids include both cis and transforms having therapeutic activity. Preferred retinoids include those having a 9-cis double bond, a 13-cis double bond or a 13-trans double bond.

The term "substituted", as used herein, means that one or more hydrogens on the designated atom are replaced with a selection from the indicated groups, provided that the designated atom's normal valency is not exceeded, and that the substitution results in a stable compound.

The substituted phenyl and naphthyl groups of the invention can have one or more hydrogen atoms replaced with a halo, hydroxy, alkyl, alkoxy, amino, cyano or carbalkoxy group. A halo group is a halogen, and includes fluoro, chloro, bromo and iodo groups. The term alkoxy refers to an alkyl group having at least one oxygen substitutent. The term carbalkoxy refers to groups of the formula —R—C(O)O— where R is an alkyl group.

As used herein "vinylogs" are desmethyl retinoyl groups having 1 or 2 additional vinyl groups relative to retinoic acid. For example such compounds include 2,6,6,-trimethyl-1-(10'-carboxy-deca-1', 3', 5', 7', 9'-pentaenyl)cyclohex-1-ene and 2,6,6-trimethyl-1-(12'-carbon-dodeca-1', 3', 5', 7', 9', 11'-hexaenyl)cyclohex-1-ene. These groups are also referred to as C20 and C22 vinylogs of desmethyl retinoic acid and are described in U.S. Pat. No. 3,882,244. The vinylogs of this invention can be prepared from a retinoyl group, any therapeutically active retinoid carboxyl group, or any group of the formula

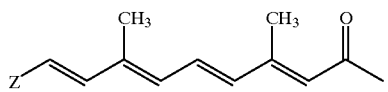

wherein Z is as defined herein.

As used herein, "therapeutically-effective amount" refers to that amount necessary to administer to a host to achieve an anti-tumor effect; to induce differentiation and/or inhibition of proliferation of malignant cancer cells, benign tumor cells or other proliferative cells; to aid in the chemoprevention of cancer; to achieve an anti-wrinkling effect; to promote wound healing or to treat a gastrointestinal disorder. Therapeutically-effective amounts can be readily determined by one of ordinary skill in the art.

As used herein and in the claims, "pharmaceutically acceptable salts and prodrugs" refer to derivatives of the disclosed compounds that are modified by making acid salts, or by modifying functional groups present in the compounds in such a way that the modifications are cleaved, either in routine manipulation or in vivo in relation to the parent compounds. Examples include, but are not limited to, mineral or organic acid salts of basic residues such as amines; acetyl, formyl and benzoyl derivatives of amines; and the like.

Pharmaceutically-acceptable salts of the compounds of the invention can be prepared by reacting the free base forms of these compounds with a stoichiometric amount of the appropriate acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference in its entirety.

The compounds provided by the present invention can be prepared generally by any method known in the art. Preparation of the novel compounds of the invention is illustrated by the following non-limiting example.

Retinoyloxymethyl Butyrate (ROBA)

A solution of retinoic acid (0.5 g, 1.67 mmol), iodomethylbutyrate (0.57 g, 1.5 eq) and $Et_3N$ (0.35 mL, 1.5 eq) in acetonitrile was stirred at room temperature overnight. The product was detected by tlc (silica plate, EtOAc:hexane 1:4) as a deep yellow spot, Rf=0.7. The solvent was removed and the residue was dissolved in EtOAc and washed with 5% $NaHCO_3$ and then with water. The oily residue, obtained after drying and solvent removal, was separated on a silica gel column (EtOAc:hexane 1:4). The product was obtained as a yellow oil (0.43 g, 64%). $^1$H-NMR ($CDCl_3$) δppm 6.99 (dd, J=15, 11 Hz, vinylic proton, 1H), 6.30 (d, J=11 Hz, vinylic proton, 1H), 6.28 (d, J=15 Hz, vinylic proton, 1H), 6.17 (s, vinylic proton, 1H), 6. 11 (d, J=5.2 Hz, vinylic proton, 1H), 5.81 (s, $OCH_2O$, 2H), 5.79 (d, J=5.7 Hz, vinylic proton, IH), 2.38 (d, J=1 Hz, Me, 3H), 2.35 (t, $CH_2CO$), 2H), 2.02 (m, $CH_2$, 2H), 2.01 (t, Me, 3H), 1.71 (s, Me, 3H), 1.65 (m,$CH_2CH_2CO$), 2H) 1.45 (m, $CH_2$, 2H), 1.03 (s, two Me's, 6H), 0.95 (t, Me, 3H), MS (CI/$CH_4$) 401 ($MH^+$), 283 ($MH^+$—$MeCH_2COOCH_2OH$ ).

The other compounds of the invention can be made in analogous fashion by substituting the appropriate iodomethylalkyl compound for iodomethylbutyrate and proceeding as generally described in the preceding paragraph. Additional methods and details for synthesis of the compounds of this invention are provided in Nudelman et al., *J. Med. Chem.* 35:687–694, 1992.

The procedures outlined above can be improved by one skilled in the art by, for instance, changing the temperature or stoichiometry of the reactions. Any such changes are intended to fall within the scope of this invention.

Utility

The compounds of the present invention are generally useful in the treatment of indications including cancer and other proliferative disorders, as differentiating agents or antiproliferative agents and in the chemoprevention of cancer.

These activities were measured using generally-accepted techniques known to those skilled in the art. For instance, the activity of compounds useful as differentiating agents can be measured using standard methodology of the nitro-blue tetrazolium reduction assay (e.g., Rabizadeh et al., *FEBS Lett.* 328:225–229, 1993; Chomienne et al., *Leuk. Res.* 10:631, 1986; and Breitman et al. in *Methods for Serum-free Culture of Neuronal and Lymphoid Cells*, Alan R. Liss, NY, p. 215–236, 1984 which are hereby incorporated by reference in their entirety) and as described below. This in vitro assay has been deemed to be predictive and in fact correlative with in vivo efficacy (Castaigne et al., *Blood* 76:1704–1709, 1990).

Another assay which is predictive of differentiating activity is the morphological examination for the presence of Auer rods and/or specific differentiation cell surface antigens in cells collected from treatment groups, as described in Chomienne et al., (*Blood* 76:1710–1717, 1990 which is hereby incorporated by reference in its entirety) and as described below.

The compounds of the present invention also have antiproliferative and anti-tumor activity. The anti-proliferation activity of compounds of the present invention can be determined by methods generally known to those skilled in the art. Two generally-accepted assays for measuring viability and anti-proliferative activity are the trypan blue exclusion test and incorporation of tritiated thymidine, also as described by Chomienne, et al., above, which is incorporated herein by reference. Another assay which is predictive and is shown to correlate with antitumor activity and in vivo efficacy is the human tumor colony forming assay described in Shoemaker et al., *Can. Res.* 45:2145–2153, 1985, which is incorporated herein by reference in its entirety. These assays are described in further detail below.

Cell Cultures

Human promyelocytic leukemia Cells (HL-60), Human Pancreatic Carcinoma Cells (PaCa-2) and Human Breast Adenocarcinoma, pleural effusion, Cells (MCF-7) were cultured as follows. Cells were grown in RPMI media with 10% FCS, supplemented with 2 Mm glutamine and incubated at 37° C. in a humidified 5% $CO_2$ incubator. Viability was determined by trypan blue exclusion. Cells were exposed to butyric acid or retinoic acid or ROBA and cultures were harvested at various time points following treatment.

Nitro-Blue Tetrazolium (NBT) Assay:

Cell differentiation was evaluated by NBT reduction activity as follows. Cell cultures containing 0.1% NBT were stimulated with 400 nM of 12-O-tetradecanoyl-phorbol-13-acetate (PMA). The cells were incubated for 30 min at 37° C. and examined microscopically by scoring at least 200 cells. The capacity for cells to reduce NBT was assessed as the percentage of cells containing intracellular reduced black formazan deposits and corrected for viability.

The results of the effect on the level of differentiation (as presented by the % NBT reduction) in HL-60 cells, by butyric acid (BA) and retinoic acid (RA) was compared with ROBA as described in Tables 1 and 2 below.

TABLE 1

Differentiation of Promyelocytic Cells

| concentration ($\mu$M) | BA (%) | RA (%) | ROBA (%) |
|---|---|---|---|
| 0 | 7 | 7 | 7 |
| 0.1 | 4 | 5 | 12 |
| 0.2 | 5 | 6 | 20 |
| 0.5 | 4 | 5 | 40 |
| 1.0 | 6 | 21 | 81 |

The results of Table 1 show that the compounds of the present invention cause HL-60 cells to differentiate in a dose dependent manner, with an increase of 81% differentiated cells. This increase is much greater than any increase seen by BA alone or RA alone.

TABLE 2

Differentiation of Promyelocytic Cells

| Concentration ($\mu$M) | NBT reduction (%) |
|---|---|
| 0 | 7 |
| RA (0.5) | 5 |
| BA (50) | 15 |
| BA (250) | 11 |
| BA (50) + RA (9.5) | 29 |
| BA (250) + RA (0.5) | 11 |
| ROBA (0.5) | 40 |
| ROBA (5) | 84 |

The results in Table 2 show that compounds of the present invention possess surprisingly superior activity than either BA alone or RA alone; and moreover, the differentiating activity of ROBA is far greater than the combination of BA plus RA.

Additional Cell Differentiation Experiment

Human promyelocytic cell line HL-60 was grown for 4 days in the presence of 0.25 $\mu$M of RA, ROBA (RN-1), retinoyloxymethylpropionate (RN-2), retinoyloxymethylisobutyrate (RN-3) or retinoyloxymethylpivalate (RN-4). The compounds were synthesized as described above. Cell differentiation was measured by the NBT assay described above. The results of two separate experiments show that ROBA, RN-2 and RN-3 significantly increased the percentage of differentiated cells in the culture relative to RA or RN-4 (FIG. 1). Table 3 shows that the average percent differentiated cells for ROBA was 73% whereas the average percent differentiated cells for RN-4 was 17%. This difference is substantial and unexpected.

TABLE 3

ROBA and RN-4 Effective on Cell Differentiation

| Compound | Exp A (%)[a] | Exp B (%) | Avg (%) |
|---|---|---|---|
| ROBA | 72 | 74 | 73 |
| RN-4 | 13 | 21 | 17 |

([a])% differentiated cells as determined by NBT reduction.

Cell Surface Antigen Immunophenotyping

Cell surface antigen immunotyping is conducted using dual-color fluorescence of cells gated according to size. The expression of a panel of antigens from early myeloid (CD33) to late myeloid is determined as described in Warrell, Jr. et al., New Engl. J. Med. 324:1385–1392, 1992, which is incorporated by reference herein in its entirety.

Northern Blot Analysis for RAR-$\alpha$ Expression

Total cellular RNA analysis is conducted by guanidinium thiocyanate phenol/chloroform extraction as described by Rabizadeh et al., FEBS Lett. 328(3):225–229, 1993, and probed with human complementary DNA (cDNA) for RAR-$\alpha$ as described by Miller et al., J. Natl. Cancer Inst. 82:1932–1933, 1990, which are incorporated by reference herein in their entireties.

Southern Blot Analysis for Genomic Rearrangements of RAR-$\alpha$

Genomic DNA is prepared and completely digested for three hours with EcoRl or HindIII (2–3 U per microgram DNA). DNA is then size fractionated on 0.8% agarose gel, denatured, renatured, neutralized and blotted onto a nitrocellulose filter. The filter is then hybridized to a 640-base pair EcoRl-Sstl cut RAR-$\alpha$ cDNA and washed stringently at 55° C. Autoradiograms are obtained after exposure at –70° C. to Kodak-XAR film with use of an intensifying screen.

Apoptosis Evaluation

Apoptosis can be evaluated by DNA fragmentation, visible changes in nuclear structure and immunocytochemical analysis of Bcl-2 expression.

DNA fragmentation is monitored by the appearance of a DNA ladder on an agarose gel. Cellular DNA is isolated by the method of Martin et al., J. Immunol., 145:1859–1867, 1990. Briefly, cells are washed twice with PBS and centrifuged at 1200 rpm at room temperature for 5 min. The pellets are resuspended at $2\times10^7$ cells/mL in lysing buffer (10 mM EDTA, 50 mM Tris, pH 8) containing 0.5% (w/v) N-laurylsarcosine and 0.5 mg/mL proteinase K and incubated for 1 h at 50° C., Heat-treated Rnase is added to a concentration of 0.25 mg/mL and incubation at 50° C. continued for 1 h. The crude DNA preparations are extracted with buffered phenol followed by two chloroform:isoamyl alcohol (24:1) extractions. DNA preparation are brought to 2.5 volumes in 10 mM Tris, pH 8, 1 mM EDTA (TE buffer) and precipitated for 24 in 2 volumes of ethanol at –70° C. The DNA precipitates are recovered by centrifugation, air dried, resuspended in TE buffer, and stored at 4° C. DNA concentration is calculated by determining the OD at 260 nm. Electrophoresis of DNA is carried out in 1% agarose gels containing 1 ug ethidium bromide as described (Martin et al.). Gels contain size markers ($\Phi\times$174 DNA HaeIII digest, 11 fragments ranging from 72–1353bp). After electrophoresis, stained gels are viewed by transillumination with UV light (302 nm) and photographed through a DS34 Polaroid direct screen instant camera using Polaroid 667 (3000 ASA) film.

Changes in nuclear structure are assessed by acridine orange staining method of Hare et al., J. Hist. Cyt., 34:215–220, 1986. Cytospins are prepared from HL-60 cells treated with BA, RA, or with one of the compounds RN-1 to RN-4. Untreated cells are used as a central. Cells are fixed with 100% ethanol for 10 min. Acridine orange (1.2 mg/mL in 0.13 M $Na_2HPO_4$, 0.35 M citric acid and 1 $\mu$M $Na_2$EDTA, pH 6.5) is applied to the fixed cells for 30 min. At least 3 fields containing about 250 cells are examined and counted under an Olympus BH-2 fluorescence microscope. The fields are photographed with an Olympus camera using Agfa film (ASA 1000).

Immunological detection of Bcl-2 is performed on untreated HL-60 cells or HL-60 cells treated with BA, RA or one of the compounds of RN-1 to RN-4. Cytospins are prepared and the cells are fixed with ethanol. Fixed cells are reacted overnight at 4° C. with the primary monoclonal antibody anti-Bcl-2 (Dako) at a dilution of 1:50. Staining is completed using Strep A-B Universal Kit (DPC, Sigma) according to manufacturer's instructions. Microscopy and photography was performed as in the preceding paragraph except that the film was ASA 200. Identically-treated cells which received no primary antibody served as non-specific binding controls.

Mouse Cancer Model

Compounds of the present invention are examined for their ability to increase the life span of animals bearing B16 melanomas, Lewis lung carcinomas and myelomonocytic leukemias described in Nudelman et al., *J. Med. Chem.* 35:687–694, 1992, or Rephaeli et al., *Int. J. Cancer* 49:66–72, 1991, which are incorporated by reference herein in their entireties.

The efficacy of compounds of the present invention in the leukemia model is tested as follows: Balb/c mice are injected with WEHI cells and drug or control solution is administered the following day. The life span of the treated animals is compared to that of untreated animals.

The efficacy of compounds of the present invention on primary tumors is tested in subcutaneously implanted lung carcinoma or B16 melanoma by measuring the mass of the tumor at the site of implantation every two weeks in control and drug-treated animals.

Chemoprevention

The chemoprevention activity of the compounds of the invention can be determined in the two-stage mouse carcinogenesis model of Nishimo et al. (supra).

Xenografts

Colon adenocarcinoma (human HCT-15 cells), mammary adenocarcinoma (human MX-1 cells) and melanoma (murine B16) xenografts are made by implanting the respective cells subcutaneously into athymic mice. Treatment with control solution or a compound of Formula (I) begins when tumors are approximately 100 mg. Anti-tumor activity is assessed by the delay in tumor growth.

Compounds of Formula (I), their salts or metabolites, can be measured in a biological sample by any method known to those skilled in the art of pharmacology, clinical chemistry or the like. Such methods for measuring compounds of Formula (I) are standard methods and include, but are not limited to high performance liquid chromatography (HPLC), gas chromatography (GC), gas chromatography mass spectroscopy (GC-MS), radioimmunoassay (RIA), and others.

Dosage and Formulation

The compounds of the present invention can be administered to treat cancer or other proliferating disorders by any means that produces contact of the active agent with the agent's site of action in the body of a subject. They can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice. The pharmaceutical compositions of the invention may be adapted for oral, parenteral, transdermal or transmucosal administration, and may be in unit dosage form, as is well known to those skilled in the pharmaceutical art. The term "parenteral" as used herein includes subcutaneous, intravenous, intramuscular, or intrasternal injection or infusion techniques.

The appropriate dosage administered in any given case will, of course, vary depending upon known factors, such as the pharmacodynamic characteristics of the particular agent and its mode and route of administration; the age, general health, metabolism, weight of the recipient and other factors which influence response to the compound; the nature and extent of the symptoms; the kind of concurrent treatment; the frequency of treatment; and the effect desired. A daily dosage of active ingredient can be expected to be about 0.001 to 1000 milligrams per. kilogram (mg/kg) of body weight, with the preferred dose being 0.05–50 mg/kg.

Dosage forms (compositions suitable for administration) contain from about 1 mg to about 1 g of active ingredient per unit. In these pharmaceutical compositions the active ingredient will ordinarily be present in an amount of about 0.5–95% by weight based on the total weight of the composition.

The active ingredient can be administered orally in solid or semi-solid dosage forms, such as for example hard or soft-gelatin capsules, tablets, and powders, or in liquid dosage forms, such as elixirs, syrups, disperse powders or granules, emulsions, and aqueous or oily suspensions. It can also be administered parenterally, in sterile liquid dosage forms. Other dosage forms are potentially possible, such as but not limited to, administered transdermally, via a patch mechanism or ointment.

Compositions intended for oral use may be prepared according to any methods known to the art for the manufacture of pharmaceutical compositions and such compositions may contain one or more agents including sweetening agents, flavoring agents, coloring agents, and preserving agents in order to provide a pharmaceutically elegant and palatable preparation.

Tablets contain the active ingredient in admixture with non-toxic pharmaceutically acceptable excipients which are suitable for the manufacture of tablets. Such excipients may include, for example, inert diluents, such as calcium phosphate, calcium carbonate, sodium carbonate, sodium phosphate, or lactose; granulating disintegrating agents, for example, maize starch or alginic acid; binding agents, such as starch, gelatin, or acacia; and lubricating agents, for example, magnesium stearate, stearic acids or talc. Compressed tablets may be uncoated or may be sugar coated or film coated by known techniques to mask any unpleasant taste and protect the tablet from the atmosphere, or enteric coated for selective disintegration and adsorption in the gastrointestinal tract.

Hard gelatin capsules or liquid filled soft gelatin capsules contain the active ingredient and inert powdered or liquid carriers, such as, but not limited to calcium carbonate, calcium phosphate, kaolin, lactose, lecithin starch, cellulose derivatives, magnesium stearate, stearic acid, arachis oil, liquid paraffin, olive oil, pharmaceutically-accepted synthetic oils and other diluents suitable for the manufacture of capsules. Both tablets and capsules can be manufactured as sustained release-products to provide for continuous release of medication over a period of hours.

Aqueous suspensions contain the active compound in admixture with excipients suitable for the manufacture of aqueous suspensions. Such excipients are suspending agents, e.g., sodium carboxymethylcellulose, methylcellulose, hydroxypropylmethylcellulose, sodium alginate, polyvinylpyrrolidone, gum tragacanth, and gum acacia; dispersing or wetting agents, such as a naturally occurring phosphatide, e.g., lecithin, or condensation products of an alkylene oxide with fatty acids, for example of polyoxyethylene stearate, or a condensation products of ethylene oxide with long chain aliphatic alcohols, e.g., heptadecaethyleneoxycetanol, or condensation products of ethylene oxide with partial esters derived from fatty acids and a hexitol, e.g., polyoxyethylene sorbitol monooleate, or a condensation product of ethylene oxide with partial esters derived from fatty acids and hexitol anhydrides, e.g., polyoxyethylene sorbitan monooleate. The aqueous suspensions can also contain one or more preservatives, for example ethyl, n-propyl, or p-hydroxy benzoate, one or more coloring agents, one or more flavoring agents, and one or more sweetening agents, such as sucrose, saccharin, or sodium or calcium cyclamate.

Disperse powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents, can also be present.

Syrups and elixirs can be formulated with sweetening agents, such as glycerol, sorbitol or sucrose. Such formulations may also contain a demulcent, a preservative and flavoring and coloring agents.

The pharmaceutical compositions can be in the form of a sterile injectable preparation, for example, as a sterile injectable aqueous suspension. This suspension can be formulated according to the known art using those suitable dispersing or wetting agents and suspending agents which have been mentioned above. The sterile injectable preparation can also be a sterile injectable solution or suspension in a nontoxic parenterally-acceptable diluent or solvent, for example, as a solution in 1,3-butane diol.

In general, water, a suitable oil, saline, aqueous dextrose (glucose), polysorbate and related sugar solutions, emulsions, such as INTRALIPID® (Cutter Laboratories, Inc., Berkley Calif. and glycols such as propylene glycol or polyethylene glycols are suitable carriers for parenteral solutions. Antioxidizing agents, such as but not limited to sodium bisulfite, sodium sulfite, or ascorbic acid, either alone or combined, are suitable stabilizing agents. Also used can be citric acid and its salts and sodium EDTA. In addition, parenteral solutions can contain preservatives, such as but not limited to benzalkonium chloride, methyl- or propylparaben, and chlorobutanol.

The pharmaceutical compositions of the present invention also include compositions for delivery across cutaneous or mucosal epithelia including transdermal, intranasal, sublingual, buccal, and rectal administration. Such compositions may be part of a transdermal device, patch, topical formulation, gel, etc., with appropriate excipients. Thus, the compounds of the present invention can be compounded with a penetration-enhancing agent such as 1-n-dodecylazacyclopentan-2-one or the other penetration-enhancing agents disclosed in U.S. Pat. Nos. 3,991,203 and 4,122,170 which are hereby incorporated by reference in their entirety to describe penetration-enhancing agents which can be included in the transdermal or intranasal compositions of this invention.

Suitable pharmaceutical carriers are described in *Remington's Pharmaceutical Sciences,* Mack Publishing Company, a standard reference text in this field, which is incorporated herein by reference in its entirety.

Useful pharmaceutical dosage-forms for administration of the compounds of this invention can be illustrated as follows:

Capsules

A large number of unit capsules are prepared by filling standard two-piece hard gelatin capsules each with 0.1–50 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, lecithin, cottonseed oil or olive oil is prepared and injected by means of a positive displacement pump into gelatin to form soft gelatin capsules containing 0.1–50 milligrams of the active ingredient. The capsules are washed and dried.

Tablets

A large number of tablets are prepared by conventional procedures so that the dosage unit was 0.1–50 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Various modifications of the invention in additions to those shown and described herein will be apparent to those skilled in the art from the foregoing description. Such modifications are also intended to fall within the scope of the appended claims.

The foregoing disclosure includes all the information deemed essential to enable those skilled in the art to practice the claimed invention. Because the cited patents or publications may provide further useful information these cited materials are hereby incorporated by reference in their entirety.

We claim:

1. A method of treating gastrointestinal disorders which comprises administering a therapeutically-effective amount of a compound represented by Formula (I) to a subject, wherein Formula (I) is

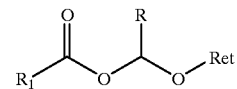

and wherein:

Ret is selected from the group consisting of retinoyl group, a therapeutically-active retinoid carboxyl group, a group represented by the formula

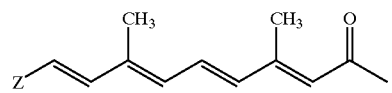

and retinoids which are C20 and C22 desmethyl vinylogs of said groups, wherein Z is a substituted or unsubstituted phenyl group, a substituted or unsubstituted naphthyl group or a cyclohexenyl group, and said phenyl or naphthyl group is substituted with from 0 to 5 substitutents selected from the group consisting of halo, hydroxy, alkyl, alkyoxy, amino, cyano or carbalkoxy, and wherein double bonds in the polyene chain of any of said groups can have a cis or trans configuration;

R is H or saturated or unsaturated group of $C_1$ to $C_5$ alkyl;

$R_1$ is ethyl, n-propyl or isopropyl;

or a pharmaceutically-acceptable salt thereof, with the proviso that when Ret is 13-cis-retinoyl and $R_1$, is n-propyl, then R cannot be H or $C_1$ to $C_5$ alkyl.

2. A method of treating cutaneous ulcers which comprises administering a therapeutically-effective amount of a compound represented by Formula (I) to a subject, wherein Formula (I) is

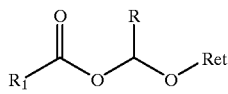

and wherein:
  Ret is selected from the group consisting of retinoyl group, a therapeutically-active retinoid carboxyl group, a group represented by the formula

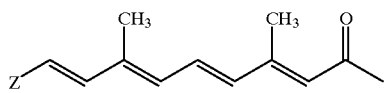

and retinoids which are C20 and C22 desmethyl vinylogs of said groups, wherein Z is a substituted or unsubstituted phenyl group, a substituted or unsubstituted naphthyl group or a cyclohexenyl group, and said phenyl or naphthyl group is substituted with from 0 to 5 substitutents selected from the group consisting of halo, hydroxy, alkyl, alkyoxy, amino, cyano or carbalkoxy, and wherein double bonds in the polyene chain of any of said groups can have a cis or trans configuration;

R is H or saturated or unsaturated group of $C_1$ to $C_5$ alkyl;
  $R_1$ is ethyl, n-propyl or isopropyl;
  or a pharmaceutically-acceptable salt thereof, with the proviso that when Ret is 13-cis-retinoyl and $R_1$, is n-propyl, then R cannot be H or $C_1$ to $C_5$ alkyl.

3. A method of inducing wound healing which comprises administering a therapeutically-effective amount of a compound represented by Formula (I) to a subject,
  wherein Formula (I) is

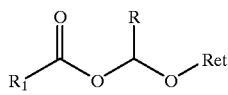

and wherein:
  Ret is selected from the group consisting of retinoyl group, a therapeutically-active retinoid carboxyl group, a group represented by the formula

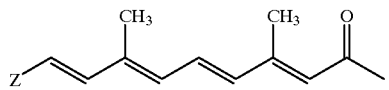

and retinoids which are C20 and C22 desmethyl vinylogs of said groups, wherein Z is a substituted or unsubstituted phenyl group, a substituted or unsubstituted naphthyl group or a cyclohexenyl group, and said phenyl or naphthyl group is substituted with from 0 to 5 substitutents selected from the group consisting of halo, hydroxy, alkyl, alkyoxy, amino, cyano or carbalkoxy, and wherein double bonds in the polyene chain of any of said groups can have a cis or trans configuration;

R is H or saturated or unsaturated group of $C_1$ to $C_5$ alkyl;
  $R_1$ is ethyl, n-propyl or isopropyl;
  or a pharmaceutically-acceptable salt thereof, with the proviso that when Ret is 13-cis-retinoyl and $R_1$, is n-propyl, then R cannot be H or $C_1$ to $C_5$ alkyl.

4. The method of any one of claims 1–3 wherein said compound is administered orally, parenterally, transdermally or transmucosally.

5. The method of any one of claims 1–3, wherein said Ret group has a 13-trans double bond.

6. The method of any one of claims 1–3, wherein $R_1$ is n-propyl.

7. The method of any one of claims 1–3, wherein said compound is 13-trans-retinoyloxymethylbutyrate.

8. The method of any one of claims 1–3, wherein $R_1$ is isopropyl.

9. The method of any one of claims 1–3, wherein said compound is 13-trans-retinoyloxymethylisobutyrate.

10. The method of any one of claims 1–3, wherein $R_1$ is ethyl.

11. The method of any on of claims 1–3, wherein said compound is 13-trans-retinoyloxymethylpropionate.

* * * * *